(12) United States Patent
Yao et al.

(10) Patent No.: US 11,806,082 B2
(45) Date of Patent: Nov. 7, 2023

(54) REMOTE OPERATIONS SYSTEM

(71) Applicant: University of Strathclyde, Glasgow (GB)

(72) Inventors: Wei Yao, Glasgow (GB); Hariprashanth Elangovan, Glasgow (GB); Ahmad Nazmi Bin Ahmad Fuad, Glasgow (GB)

(73) Assignee: UNIVERSITY OF STRATHCLYDE, Glasgow (GB)

( * ) Notice: Subject to any disclaimer, the term of this patent is extended or adjusted under 35 U.S.C. 154(b) by 653 days.

(21) Appl. No.: 15/580,825

(22) PCT Filed: Jun. 7, 2016

(86) PCT No.: PCT/GB2016/051673
§ 371 (c)(1),
(2) Date: Dec. 8, 2017

(87) PCT Pub. No.: WO2016/198844
PCT Pub. Date: Dec. 15, 2016

(65) Prior Publication Data
US 2018/0338796 A1    Nov. 29, 2018

(30) Foreign Application Priority Data
Jun. 8, 2015 (GB) .................................. 1509887

(51) Int. Cl.
*A61B 34/20* (2016.01)
*A61B 34/30* (2016.01)
(Continued)

(52) U.S. Cl.
CPC .......... *A61B 34/20* (2016.02); *A61B 17/1626* (2013.01); *A61B 34/30* (2016.02);
(Continued)

(58) Field of Classification Search
CPC ...... A61B 17/1622–1633; A61B 17/16; A61B 17/17; A61B 17/1703; A61B 17/1707; A61B 2017/1602
See application file for complete search history.

(56) References Cited

U.S. PATENT DOCUMENTS 5,086,401 A * 2/1992 Glassman .............. A61B 34/30
606/88
2002/0151784 A1    10/2002 Mizoguchi et al.
(Continued)

FOREIGN PATENT DOCUMENTS

| EP | 1566150 A2 | 5/2005 |
| EP | 1566150 A3 | 3/2006 |

(Continued)

OTHER PUBLICATIONS

International Searching Authority, International Search Report and Written Opinion for International Application No. PCT/GB2016/051673, dated Sep. 19, 2016, 15 pages, European Patent Office, Netherlands.

(Continued)

*Primary Examiner* — Amy R Sipp
(74) *Attorney, Agent, or Firm* — Alston & Bird LLP

(57) ABSTRACT

A surgical system having an arm or elongate portion, the arm or elongate portion being bendable, articulated, reconfigurable and/or flexible such that the arm or elongate portion is steerable by bending, articulating, reconfiguring and/or flexing of the arm. The arm or elongate portion includes or is configured to receive at least one tool or load. The system includes one or more first and/or second location or position tracking systems that are configured to determine and/or track a location and/or position of one or more parts or a whole of the arm or elongate portion and/or the tool or load. The at least one first location or position tracking system is a non-optical or non-radiation based location or positioning (Continued)

tracking system. The second location or position tracking system is an optical or radiation based positioning system. The system includes or is configured to implement or configured to communicate with a navigation platform for facilitating navigation and/or operation of the system using the location and/or position obtained from the one or more first and/or second location or position tracking systems.

38 Claims, 7 Drawing Sheets

(51) Int. Cl.
    *A61B 17/16*     (2006.01)
    *A61B 34/10*     (2016.01)
    *A61B 90/00*     (2016.01)

(52) U.S. Cl.
    CPC . *A61B 2017/1602* (2013.01); *A61B 2034/102* (2016.02); *A61B 2034/107* (2016.02); *A61B 2034/2055* (2016.02); *A61B 2034/2059* (2016.02); *A61B 2090/0818* (2016.02)

(56) References Cited

U.S. PATENT DOCUMENTS

| | | | |
|---|---|---|---|
| 2006/0142657 A1* | 6/2006 | Quaid | A61B 17/1703 600/424 |
| 2007/0013783 A1 | 1/2007 | Goldbach | |
| 2011/0319912 A1* | 12/2011 | Nishio | A61B 17/1631 606/130 |
| 2012/0157887 A1* | 6/2012 | Fanson | A61F 2/32 600/595 |
| 2014/0163736 A1 | 6/2014 | Azizian et al. | |
| 2014/0378999 A1 | 12/2014 | Crawford et al. | |
| 2015/0045656 A1 | 2/2015 | Yoon et al. | |

FOREIGN PATENT DOCUMENTS

| | | |
|---|---|---|
| KR | 20100098055 A | 9/2010 |
| WO | WO 2014/151550 A2 | 9/2014 |

OTHER PUBLICATIONS

The International Bureau of WIPO, International Preliminary Report on Patentability (Chapter I) for International Application No. PCT/GB2016/051673, dated Dec. 21, 2017, 11 pages, Switzerland.

European Patent Office, Communication pursuant to Article 94(3) EPC, dated Jun. 3, 2006, 9 pages, Netherlands.

European Patent Office, Communication pursuant to Article 94(3) EPC received for Application No. 16729969.2, dated Jun. 3, 2006, 9 pages, Netherlands. (Previously submitted and considered, added the Application No. to the description.)

European Patent Office, Summons to Attend Oral Proceeding received for Application No. 16729969.2, dated Mar. 9, 2021, 7 pages, Netherlands.

* cited by examiner

US 11,806,082 B2

REMOTE OPERATIONS SYSTEM

CROSS REFERENCE TO RELATED APPLICATIONS

This application is a National Stage Application, filed under 35 U.S.C. 371, of International Application No. PCT/GB2016/051673, filed Jun. 7, 2016, which claims priority to United Kingdom Application No. 1509887.4, filed Jun. 8, 2015; the contents of both of which as are hereby incorporated by reference in their entirety.

BACKGROUND

Related Field

The present invention relates to a remote operation system, such as a robotic surgical system, particularly but not exclusively to a medical device, such as a bone drill for drilling bones of a patient, a method of using said device, a use of said device and a kit comprising the device and a processing system and computer program product for at least partially implementing the device and/or method.

Description of Related Art

Surgical robotic technology has been developed to increase the accuracy of surgery, minimise post-surgical complications and improve patient outcomes. Computer-Aided Orthopaedic Surgery (CAOS) employs robotic surgical devices and navigation systems to improve the surgical field visibility and enhance the accuracy of the use of surgical tools in surgical procedures.

Advances in radiographic imaging have enabled reconstruction of images into 3D models that can be used in surgical pre-operative planning to plan diverse surgical procedures. The digital 3D models serve as a navigation map for the procedures, allowing virtual visualisation of surgical tools and the anatomy being operated on in real time. Employing this methodology improves the accuracy and precision of the surgery and provides the surgeon with a better and wider view of the surgical field.

The advent of Computer-Aided Surgery (CAS) and robotic surgical devices has improved the field of Minimal Invasive Surgery (MIS) through free manoeuvrability of the instrument, sensory feedback and three-dimensional imaging. However, to date there are no tools available that provide sufficient precision and force transformation for bone milling in orthopaedic surgery.

Providing a flexible, steerable robotic device capable of milling curved profiles or pathways in bones and other anatomy pathways in the body within constrained spaces may be beneficial for the prevention of intra-operative fractures, providing a better fit, fill and alignment of the prostheses and reducing the trauma.

BRIEF SUMMARY

Aspects of the invention are defined by the independent claims appended herewith. One or more preferable features of the invention are defined by the dependent claims appended herewith.

According to a first aspect of the invention there is provided a remote operations system, such as a robotic surgical system, which may be or comprise or be comprised in a surgical drill or bone drill. The system may comprise at least one location or position tracking system, which may comprise an optical tracking device. The system may comprise a navigation platform. The navigation platform may facilitate navigation and operation of the system using position data obtained from the location or position tracking system. The device may be or comprise a surgical drill for drilling/milling a patient's bone accurately. However, it will be appreciated that it may also be applied to other instruments, particularly to surgical instruments.

The remote operations system may comprise a flexible, articulated and/or bendable device. The device may be steerable. The system may be or be integrated into a robotic system, such as a robotic surgical system. At least part of the device may be configurable to move, bend, articulate and/or drill straight and/or curved profiles.

The device may comprise an arm or elongate portion. The arm or elongate portion may be bendable, articulated, reconfigurable and/or flexible. The arm or elongate portion may be steerable, e.g. by bending, articulating, reconfiguring and/or flexing the arm. The device may comprise or be configured to receive at least one tool or load, e.g. at an end of the arm or elongate portion, such as a distal end of the arm or elongate portion. The remote operations system may comprise the one or more location or position tracking systems, which may be configured to determine and track a location and/or position of one or more parts or a whole of the device and/or the tool or load. The location or position tracking system may be or comprise a hybrid location or position tracking system. The location or position tracking systems may comprise at least first and second location or position tracking systems, which may be different types or categories of location or position tracking systems, and/or use different location or positioning technology or techniques. At least the first location or position tracking system may be or comprise a non-optical or non-radiation based positioning system. At least the second location or position tracking system may be or comprise an optical or radiation based positioning system.

By providing a load or tool on the distal end of the arm, which may be articulated, bent or flexed in order to steer the arm, then it is possible to carry out operations using the tool or load at locations that are remote from a proximal end of the arm. By providing a non-optical or non-radiation based position or location tracking system, the position or location of the distal end of the arm and/or the tool or load can be tracked during the operations, even when the arm, tool or load is located in the body and particularly inside a bone that may otherwise prevent the use of, or reduce the effectiveness of, optical and/or radiation based location tracking systems. By providing two different types of location or position tracking systems, e.g. both a non-optical/non radiation based location or position tracking system, which may be provided at the distal end of the arm, and an optical or radiation based tracking system, which may provide 6 degrees of freedom at the base of the device, then absolute and/or more accurate determination of the location of the arm and/or tool or load may be determined. Particularly, the position of the arm and/or tool or load relative to other objects such as the bone and/or a prosthesis may be determined.

The tool may be or comprise a medical or surgical device, such as a drill chuck, drill bit and/or drill system, e.g. for drilling bone. The drill bit may be attached or attachable to the arm by means of a drill chuck. The drill bit may comprise a metal rod. The drill bit may be connected to the distal end of the flexible shaft.

The device may be configured to fit within a small incision in the bone. For example, at least part of the system, e.g. the arm and/or the tool or load, may have a maximum diameter of less than 10 mm. At least part of the device, e.g. the arm, may be capable of bending to curved profiles. The device may be robust. At least part of the device, e.g. the segments or portions of the arm, may be constructed from metal, e.g. surgical steel. This may prevent movement or displacement of the base of the device, e.g. while drilling bone, for example while drilling a curved profile in a bone.

The surgical drill may be configured to drill any type of bone, such as femur, tibia, fibula, patella, sinuses, neck bones, buccal bones, skull bones, tooth and the like.

The arm or elongate portion may be segmented and/or comprise a plurality of segments or portions. At least one or each segment or portion may be or comprise an elongate segment or portion and/or may be or comprise a rigid segment or portion. At least one or each of the segments or portions may be movable, rotatable, articulated, reorientatable and/or reconfigurable relative to one or more or each other segment or portion, e.g. relative to one, two or more adjacent segments or portions. The arm or elongate portion may comprise at least one a joint or pivot, which may be provided between at least one or more or each segment or portion and at least one other segment or portion, such as between one or more adjacent segments or portions. At least one or each joint may comprise a rotatable or revolute joint.

The arm may comprise a kinematic chain. The kinematic chain may comprise multiple links, wherein each link may be or comprise one or more of the segments or portions of the arm. For example, the kinematic chain may comprise 2, 3, 4, or 5 links or segments or portions. The number of segments or portions of the arm, e.g. the number of links of the kinematic chain, may depend on the length of the channel to be drilled or on the degree of curvature of the channel. One, two or more of the links may be connected only to one other link, that is, one, two or more the links may be singular links. One or more of the links may be connected to two other links, that is, one or more of the links may be binary links. Each binary link may be assembled in the kinematic chain by revolute joints. Each link may be configured to rotate with respect to the other links of the kinematic chain. For example, a kinematic chain comprising three links may allow for rotation of each link with respect to the other two links.

The links (e.g. the segments or portions) may be hollow. The links may accommodate a flexible shaft. The tool or load (e.g. the drill bit, chuck or bur) may be attached, mounted or mountable to an end, such as a distal end of the arm or elongate portion of the device. Each link may be connected by mechanical fasteners (e.g. the joints) configured to allow free rotation of the joint. For example, each link may be connected by two rivets. Each link connection (e.g. joint) may comprise one or more bearings. For example, each link connection (e.g. joint) may comprise two or more bearings. The bearings may be or comprise ball bearings. The bearings may be or comprise high-speed micro ball bearings. Advantageously, the bearings may reduce the friction and may limit temperature increase of the kinematic chain upon bending, articulation or rotation.

The arm or elongate portion may comprise or be configured to receive a sheath or cover, which may be disposed or disposable on an outer surface of part or all of the arm. The sheath or cover may comprise a biocompatible material. The sheath may be washable. The sheath may be removable and/or replaceable. The sheath may be disposable.

The arm or elongate portion may comprise or be configured to receive or engage with at least one actuating or moving mechanism for moving, rotating, articulating, reorienting and/or reconfiguring at least one or each of the segments or portions relative to at least one or each other of the segments or portions. At least one of the segments and/or portions may be actively movable, rotatable, articulated, reorientatable and/or reconfigurable relative to at least one other of the segments and/or portions, e.g. directly responsive to the at least one actuating or moving mechanism. At least one of the segments and/or portions may be passively movable, rotatable, reorientatable, articulated and/or reconfigurable relative to at least one other of the segments and/or portions, e.g. responsive to motion of the at least one actively movable, rotatable, reorientatable and/or reconfigurable segment and/or portion. At least part of the device, e.g. the arm or elongate portion, may be steerable, bendable, articulated or reconfigurable by movement of the one or more or each segment relative to the at least one or more or each other segment, e.g. using the at least one moving or actuating mechanism.

The arm may be configured to bend through one or more degrees of freedom. This may be advantageous because it may allow the drill arm to navigate through the incision while drilling the bone. The device may be rotatable, twistable or configured to rotate, e.g. to provide additional degrees of freedom. Twist or rotational motion of the arm may be achieved manually, for example by twisting the base of the device.

The remote operations system may comprise at least one motor or actuator. At least one of the motors or actuators may be configured to operate the tool or load. At least one of the motors or actuators may be configured to operate the at least one actuating or moving mechanism.

The remote operations system may comprise a control unit. The proximal end of the arm may be connected to the control unit, where the arm is attached. Within the context of the present invention the proximal end of the arm may be the opposite end to the end on which the tool or load, e.g. the drill bit, is located or locatable. The control unit may comprise the at least one motor or actuator. The motor(s) may be or comprise a servo motor. The motor(s) may be or comprise a high torque motor. High torque servo motors may be advantageous because they may provide sustained bending of the arm, e.g. while maintaining an operation such as a bone milling/drilling action.

The control unit may comprise a controller, which may comprise a microcontroller board, for example. The controller may control the at least one motor or actuator.

The device, e.g. the control unit of the device, may comprise or be configured to receive or communicate with a control system. The control system may be fully actuated. The control system may be dexterous. The control system or actuator may be located on the control unit. The control system may be operable to control operation of the tool or load. The control system may be operable to control the at least one of the actuating or moving mechanisms. The control system may be configured to allow the user to steer the device, e.g. the arm of the device, or the tool or load, such as the drill. The control system may be configured to control bending of the arm and/or the moving, rotating, reorienting, articulating and/or reconfiguring of the at least one or each segment or portion of the arm relative to the at least one or each other segment or portion of the arm. The control system may be of any suitable shape or form. For example, the control system may comprise any one of a control stick, buttons, touch screen, a control wheel and/or the like. The control system may be or comprise a haptic control system.

The at least one moving or actuating mechanism may comprise one or more control members, e.g. flexible control members, which may be or comprise one or more wires or shafts. The one or more control members may run within at least one or more or each of the hollow segments or portions. At least one or each of the control members may run between the control system and a corresponding segment or portion of the arm. One end of at least one or each of the one or more control members may be connected to the corresponding segment or portion. At least one or more or each of the segments or portions may be movable, rotatable, reorientatable, articulatable and/or reconfigurable relative to one or more or each other segment or portion via operation of the respective or associated control member. The drill arm may be configured to be actuated or steered by means of the control members. The drill arm may comprise wire-driven steering capability. For example, the segments or portions of the arm (i.e. the joints of the kinematic chain) may be configured to be rotated or articulated by the control members. Wire-driven steering may be advantageous because it requires little space for actuation, enables smooth actuation and actuation in curved configurations. The control members may be configured to rotate or articulate the joints of the arm clockwise and/or counter-clockwise.

The control members may be located inside the kinematic chain. The control members may be located outside a flexible drive member or shaft. The flexible drive member or shaft may be for operating or driving the tool, such as the drill or drill chuck. The control members may be or comprise steel wires. The control members may be or comprise braided wires. The control members may have any suitable tensile limit. For example, the tensile limit of the control members may be 30, 40, 50, 60 or 70 pounds of force. The distal end of at least one of the control members may be anchored to the distal end of the device. At least one of the control members may be anchored to the tool or load end of the device. At least the distal segment or portion of the arm (e.g. the distal link of the kinematic chain) may be actively actuated, rotated, actuated or moved by the control member. One or more or each of the other links may be passively actuated, rotated, actuated or moved, e.g. by the bending of the distal link. The proximal end of the control member(s) may be connected to at least one of the motors or actuators.

The at least one first location or position tracking system may comprise one or more bend, rotation or angular sensors for measuring the bend or rotation of at least part of the arm and/or a relative angle or orientation between at least two segments or portions or between each segment or portion. At least one bend, rotation or angular sensor may be provided to measure the relative angle or orientation between the segments or portions of at least one or each pair of adjacent segments or portions. The bend, rotation or angular sensor may comprise a rotary or angular encoder. One or more dimensions, e.g. the length, of one or more or each segment or portion of the arm may be known, e.g. predetermined, and may be stored in and/or accessible from a memory. The remote operations system may comprise or be configured to communicate with a processing device. The processing device may be configured to determine the location or position of at least one or more or each point along at least part or all of the device, e.g. the arm or elongate portion of the device, and/or of the tool or load, e.g. using the measured relative angle or position of at least one or each pair of adjacent segments or portions and/or the one or more dimensions, e.g. length and optionally the width and/or diameter, of at least one or each segment or portion.

In this way, the processing device may be configured to determine the position of the arm or elongate portion and/or of the tool or load, e.g. in 3D, based on the measured relative angle between segments and portions of at least one or each pair of adjacent segments or portions and/or the length or at least one or each segment or portion, for example, by applying a transformation matrix, such as a homogeneous transformation matrix, and/or by using geometrical techniques that would be apparent to a skilled person from the present teaching. As such, the processing device may be configured to determine the position of the arm or elongate portion or at least one or more points thereon and/or the tool or load even when the arm or elongate portion and/or tool or load is within the body and more particularly within a bone, which may prevent the use of other techniques, such as optical or other radiation based techniques for determining the location of the arm or elongate portion and/or tool or load.

At least one of the bend or angular sensors may comprise a potentiometer, such as a button potentiometer. At least one of the bend or angular sensors may be configured to provide a variable voltage and/or resistance that depends on the relative angle, e.g. between two connected or adjacent segments or portions. The device may comprise at least one analog-to-digital converter, which may be configured to digitise an analogue output of the at least one bend or angular sensor. The processing device may comprise or be configured to access a map or look-up table or equation or other conversion means for determining the corresponding relative angle from the output (e.g. the digitised output) of the at least one bend or angle sensor.

The at least one first position or location tracking system may comprise the bend or angular sensors located at each joint. The at least one first position or location tracking system may be operable to track the distal end of the device, e.g. of the arm, and/or the tool or load. The bend or angular sensors may be configured to track the rotation, articulation and/or bending angle of at least one or each joint and may thereby track and/or determine the position of at least part or all of the arm, such as the distal end of the arm and/or the load or tool. The tracking may be with reference to the proximate end of the device, e.g. the control unit and/or the reference point or part of the device. The position of the distal end of the device, e.g. of the arm, may be determined by forward kinematics.

Advantageously, the first position or location tracking system may act as an extension for the second position or location tracking system when the distal end of the device (e.g. of the arm) and/or the tool or load is not visible, e.g. when they are inside the drill hole. As such, the second position or location tracking system may be configured to track the proximal end of the device and/or the reference point or part of the device, e.g. of the arm, and optionally the bone while the first position or location tracking system may be configured to track the distal end of the device, e.g. of the arm, or the tool or load.

The at least one second or further location or position tracking system may be for determining a location or position of at least part of the device, such as a part of the device that is outwith the body and/or bone, e.g. in use. The at least one second or further location or positioning tracking system may comprise an optical or other radiation based position or location tracking system, such as an Infra-red (IR) based location or position tracking system. The at least one second or further location or position tracking system may be configured to determine and/or track the position or location of the at least one reference point or part of the device. The processing device and/or the first location or position tracking system may be configured to determine the location or position of the at least one or more or each point along at least part or all of the device, e.g. the arm or elongate portion of the device, and/or the tool or load relative to the location or position of the at least one reference point or part of the device determined by or using the at least one second or further location or position tracking system. The reference point or part of the device may be or comprise or be provided on or with reference to a part of the device that is outwith the body and/or bone in use, e.g. a control or motor device, box or unit. In this way, the location or position of the reference point or part can be determined using the second location or position tracking system and the location or position of at least part of the arm and/or the tool or device with reference to the reference position or location can be determined using the first location or position tracking system.

The second or further location or position tracking system may comprise at least one base station and one or more tracked units. The base station may be fixed. The second or further location or position system may be configured to track the position of the one or more tracked units, e.g. relative to the base station. At least one of the one or more tracked units may be coupled to or mounted or provided on or in the device, which may be at the proximate end of the device, e.g. on or in the control system, control unit or another part of the device that is outside the body and/or bone in use, e.g. at the reference point or part of the detector. At least one of the one or more tracked units may be mounted on another medical or surgical device or tool.

The second or further location or position tracking system, e.g. the base station and/or the one or more tracked units, may comprise at least one sensor, such as an optical or radiation sensor or detector, e.g. a camera. The second or further location or position tracking system may be configured to track at least part of the device outside the drill hole, body and/or bone. The second or further location or position tracking system, e.g. the base station and/or the one or more tracked units, may comprise at least one, and preferably two or more, radiation and/or light emitters and/or at least one radiation or light detector. The radiation and/or light emitter may comprise an LED, such as an infrared LED.

The radiation or light emitters may be located remotely from the drill arm. The radiation or light emitters may be configured to act as a stationary reference plane. The radiation or light emitters may be located on or attached to surgical objects.

The radiation or light detectors may be attached to surgical objects and/or the device. The radiation or light detectors may be located remotely from the drill arm.

The radiation or light sensors or detectors may comprise a camera. For example, the cameras may be infrared cameras. The cameras may be configured or operable to provide 6 Degree of Freedom tracking information.

The light or radiation sensors or detectors may be or comprise a micro infrared camera. The device may comprise two or more light or radiation sensors or detectors. The two or more light or radiation sensors or detectors may be interpolated. For example, light or radiation sensors or detectors may be interpolated to achieve a 1024×768 pixels configured to provide a frame rate up to 100 frames per second.

The remote operations system may be configured to determine and/or track the distance, angle and/or relative position of each detector and/or the part of the device associated therewith, e.g. by detecting, monitoring or sensing light or radiation emitted by the radiation and/or light emitter(s) of the base station and/or one or more tracked units, for example by using the light or radiation sensors or detectors of the one or more tracked units and/or the base station.

The base station may be stationary. The base station may be located remotely from the arm and/or tool or load. The base station may comprise at least one camera. The base station may comprise two or more radiation and/or light emitters. The base station may comprise or be configured to communicate with the processing device.

The second or further location or position system, e.g. the base station and/or the one or more tracked units, may comprise elements located on or attached to surgical equipment.

The base station may be configured to communicate with the tracked units, e.g. located on or attached to surgical equipment. The communication may comprise wireless communication. The communication may be via a link. The communication may be via a high speed, low power radio-frequency link. The communication may be via a transceiver link.

The tracked units, which may be located on or attached to the surgical equipment and/or the device may be configured to communicate with the base station in a sequenced fashion, e.g. the tracked units may each communicate with the base station in a sequence. The tracked units may be configured to communicate with the base station in a pulse coded fashion. Communication between the tracked units and the base station in a sequenced fashion may allow the base station to recognise each tracked unit individually.

The radiation or light detector of each tracked unit may be configured to receive and/or record signals emitted by the one, two or more radiation and/or light emitters of the base station. The tracked units may each comprise a tracked unit processor. The tracked unit processor may be configured to determine the location or position of the tracked unit, e.g. based on the signals emitted by the one, two or more radiation and/or light emitters of the base station, which may be received by the radiation or light detector of the tracked unit. Each tracked unit may be configured to transmit or stream its location, e.g. according or relative to the reference frame, for example a coordinate system, which may be centred or based on the base station. Each tracked unit may be configured to transmit or stream its location through the wireless link. Each tracked unit may be configured to transmit or stream its location with a unique ID, which may comprise a 24 bit ID.

The camera of the base station may be configured to receive and/or record signals emitted by the one, two or more radiation and/or light emitters of at least one or each tracked unit, e.g. located on or attached to surgical equipment and/or the device. The base station may comprise or be configured to communicate with a base station processor, which may be, or be implemented by or comprised in the processing device. The base station processor may be configured to determine the position of at least one or each tracked unit, e.g. according to the reference frame, for example a coordinate system. The coordinate system may use the location of the base station as the reference location.

The base station processor may be configured to determine the position, which may be a 3D position, of one or more or each tracked unit with reference to the base station, e.g. based on the signals emitted by the one, two or more radiation and/or light emitters of the respective tracked units, which may be received by the radiation or light detector of the base station. The base station processor may use the position and/or location of the one or more or each tracked unit, e.g. the coordinates of the one or more or each tracked unit, determined by the base station processor and/or the one or more or each tracked unit processor to determine the position, e.g. the 3D position, of the one or more or each tracked unit with respect to the base station. The base station processor and/or tracked unit processor(s) may be configured to send location coordinates to the processing device. It will be appreciated that the processing device may be comprised in the device and/or remote from the device, e.g. it may be server based or distributed. Furthermore, one or more or each of: the processing device, the base station processor and/or the tracked unit processor may be implemented by the same processing system or by different processing systems.

The optical or radiation sensor or detector, e.g. camera, of the base station may be configured to collect one or more perspective coordinate images of at least one or each of the light or radiation emitters of at least one or each tracked unit. The optical or radiation sensor or detector, e.g. camera, of at least one or each tracked unit may be configured to collect one or more perspective coordinate images of at least one or each of the light or radiation emitters of the base station. From any two of the perspective images (i.e. the perspective image collected by the base station sensor or detector and the perspective image collected by the tracked unit), in principle, the relative X, Y and Z position of the tracked unit may be calculated using principles of perspective geometry.

The tracking of the Tracking module 2 is done next by switching on the LEDs on the second module and calculating its location from the values observed from its perspective.

The processing device may comprise, be comprised in or configured to implement a tracking system for tracking at least a part, e.g. the arm and/or the tool or load, or all of the device, in use. The processing device may comprise, be comprised in or configured to implement the navigation system, e.g. for steering, moving and/or manoeuvring the device, in use. The processing device may comprise, be comprised in or configured to implement a mapping system for determining the relative positions or locations of at least part of the device, e.g. the arm and/or the tool or load, and/or a part of a patient, such as at least part of a bone, e.g. femur, of the patient and/or at least one other object, such as a medical or surgical object such as a medical or surgical tool or object, e.g. a prosthesis, implant, replacement part or the like, such as a femoral stem. The tracking system, navigation system and/or mapping system may be configured to use the location and/or position of the one or more parts or the whole of the device and/or the tool or load determined by the first and/or second location or position systems, e.g. to track, steer, move or manoeuvre at least part of the device or for determining the relative positions.

The processing device may be configured to implement or provide a viewing system or display, such as a virtual reality viewing system.

The processing device may comprise or be configured to implement a modelling system for modelling, e.g. virtually modelling, the device and optionally also one or more of the other objects, tools or devices, which may be involved in the medical, surgical or other procedure in which the device is being used. For example, the other objects, tools or devices may be or comprise at least part of the body or patient, such as the bone that is being or to be drilled or milled by the device. The other objects, tools or devices may be or comprise one or more other tools or devices, such as surgical or medical tools or devices. The modelling system may be configured to produce and/or update the model based on the positions and/or locations of the device (e.g. the arm) or one or more parts of the device (e.g. the arm), the tool or load on the arm, and/or the one or more other objects, tools or devices. At least some or all of the positions and/or locations used by the modelling system may be or comprise the positions and/or locations determined and/or tracked by the one or more (e.g. the first and/or second) location or position tracking systems. The modelling system may be configured to produce and/or update the model based on properties of the device or of the one or more other objects, tools or devices, which may comprise geometric properties or dimensions, such as length, height, width, diameter, and/or a 3D geometrical description of at least part or all of the device or of the one or more other objects, tools or devices. The modelling system may be configured to update the model in real time or near real time, e.g. during a procedure.

The tracking system, navigation system and/or mapping system may be configured to use the model in order to track, navigate, steer, move and/or map the device and/or the one or more other objects, tools or devices.

The viewing system or display (e.g. a man-machine interface) may be configured to display the position or location of the device, e.g. relative to the position or location of the one or more other objects, tools or devices, e.g. based on the positions and/or locations determined using the modelling system and/or the first and/or second position or location tracking systems. The display or viewing system may configured to guide a surgeon during a surgical procedure. The processing device may be configured to receive and/or process coordinate data, e.g. from the first and/or second location or position tracking system. The processing device may not process image data. Processing coordinate data may be faster than processing image data. Beneficially, the processing device may be configured to accommodate high tracking rates with low system memory usage and low jitter.

The navigation system may be configured to guide the surgical procedure. The navigation system may be configured to provide at least part or all of the model, e.g. from the modelling system, which may be in real time. The model may comprise models of the device, e.g. the arm, and/or the tool or load. The navigation system may be configured to provide the model of the at least one other object, tool or device, such as the bone to be drilled. The model may be or comprise a CAD model, which may be at least partially derived from a CT scan.

The navigation system may be or comprise a multi-modality computer-aided navigation system. The navigation system may comprise or be configured to access the mapping system. The mapping system may be configured to map the at least part of the device, e.g. the arm, and/or the tool or load and optionally the at least one other object, tool or device, such as the bone to be drilled. The mapping system may be configured to map a prosthesis or other surgical object, which may be for use in surgeries in which a prosthesis is to be implanted.

The model may comprise a 3D mesh model, e.g. of the at least one other object, tool or device such as the bone, the device and/or the prosthesis. The navigation system may be configured to create a virtual milling pattern in the virtual model of the at least one other object, such as the bone, e.g. as the surgery is performed. The device may be movable and/or articulated and/or reconfigurable and/or reorientatable according to the virtual milling pattern.

The viewing system or display may be configured to display the position of the device and/or prosthesis, in relation to the drilled bone. Advantageously, this may guide the surgeon to correctly locate the prosthesis in the drilled bone. The mapping system may be configured to link the different models, e.g. models of the device and models of the at least one other object, such as models of the prosthesis and bone, e.g. for allowing virtual interaction between the models. For example, the mapping system may be configurable to allow the virtual models to be moved, rotated and overlapped with other virtual models.

The 3D models may be configured to be programmed in any suitable language. For example, the 3D models may be configured to be programed in JAVA Processing language.

The mapping system may be configured or programmable to provide, set up and/or monitor a boundary, such as a boundary of safe surgical volume. Within the context of this invention, the safe surgical volume may be a volume to be milled or drilled and that may be confined within the volume of the bone 3D model. The mapping system may be configured to display a warning message when the tool or load, e.g. the drill bit, reaches, and/or approaches within a threshold limit of, the boundary. The mapping system may be configured to stop the motor or stop or change operation of the tool or load when the tool or load, e.g. the drill bit, reaches, or approaches within a threshold limit of, the boundary.

Advantageously, programming boundaries enables the user, e.g. the medical practitioner, to mill/drill the bone in the precise shape and location, for example following the shape of a prosthesis to be implanted.

The navigation system may comprise a graphical user interface. The graphical user interface may be configured to guide the user on the navigation steps to mill/drill a bone. The graphical user interface may implement or be implemented by the viewing system or display.

The graphical user interface and/or viewing system or display may support one or more of the following: 3 axis navigation panning, rotation, zooming, area zooming, return to specific camera view, 2D grid, 3 axis legend and the like.

In a second aspect of the invention there is provided a method of drilling or milling a bone with the device of the first aspect of the invention, wherein the device comprises or is comprised in a surgical drill. The method may comprise bending, articulating, reconfiguring and/or reorienting the arm of the device during the drilling or milling. The method may comprise obtaining or receiving a CT scan of the bone to be drilled. The method may comprise creating, providing or receiving a 3D model of the bone from the CT scan.

The method may comprise creating, obtaining or receiving a 3D model of a prosthesis to be implanted.

The method may comprise creating, obtaining or receiving a model of the device.

The method may comprise providing the model of the bone to the navigation system. The method may further comprise providing the model of the prosthesis and/or the coordinates and orientation information of the bone and optionally the prosthesis.

The method may comprise positioning the prosthesis model inside the 3D bone model. The method may comprise linking the coordinates of the bone model and the prosthesis model to enable virtual interaction between the models.

The method may comprise programming the safe surgical volume boundary. This may modify the 3D bone model outline to comprise the safe surgical volume boundary.

The method may comprise pre-operative planning computer assisted orthopaedic surgery (CAOS). CAOS may comprise mapping the virtual models of the bone and the prosthesis into the navigation system. Advantageously, this may enable real-time position tracking of device or other objects virtually at the screen.

The method may comprise providing the model of the surgical drill to the navigation system. The method may comprise obtaining a position or location of at least part of the device, e.g. of at least part or all of the arm of the device and/or the tool or load, which may be in the form of coordinates and/or orientation data of the device, e.g. from or using the one or more (e.g. the first and second) location or positioning tracking systems of the device. The method may comprise obtaining the position or location of at least part of the device during the drilling or milling.

The method may comprise registering the virtual models with the associated device or object using the optical tracking system. The objects may be or comprise the device, bone and prosthesis.

The method my comprise registering a joint angle tracking. The method may comprise linking the joint angle tracking with 6DOF tracking of the control unit.

The method may comprise milling the bone according to the safe surgical volume boundary. Advantageously, the drill motor may stop when the drill bit touches a boundary.

The method may comprise fitting the implant in the milled bone.

The method may be employed for any surgical procedure involving bone milling. The method may be employed in Minimally Invasive Surgery (MIS). For example, the method may be employed in total hip arthroplasty (THA). The method may be employed in tunnel drilling in anterior cruciate ligament (ACL) reconstruction, milling in revision of arthroplasty, drilling in skull and neck surgery, drilling in buccal surgery, such as buccal bone reconstructive surgery for implant site preparation, and the like.

In a third aspect of the invention there is provided the use of the surgical drill of the first aspect of the invention for drilling or milling a bone. The use may comprise drilling a hole in a bone. The use may comprise locating a prosthesis in the drilled bone. The use may comprise performing total hip arthroplasty. The use may comprise performing neck surgery, skull surgery, buccal surgery, ACL reconstruction surgery and the like.

In a fourth aspect of the invention there is provided a system or kit comprising the device (e.g. the surgical drill), the navigation system and the tracking system of the first aspect. The system or kit may comprise multiple drill bits for diverse applications. The system or kit may comprise replaceable sheaths for the drill arm. The system or kit may comprise spare links to modify the length or diameter of the kinematic chain of the drill arm. The system or kit may comprise equipment for disinfecting the drill after its use. The system or kit may comprise software configured to load the navigation system in the user's computer. The system or kit may comprise a prosthesis for implantation after the drilling action.

According to a fifth aspect of the invention is a location or position tracking system, which may be for determining a location or position of an object or device. The object or device may be or comprise part of a surgical tool or device, such as at least a part of an arm of a remote operations device, and/or a tool or load carried thereby. The location or position tracking system may be comprised or configured for use in the system of the first aspect. The device and/or tool or load may be or comprise the device and/or tool or load described in relation to the first aspect. The location or position tracking system may be or comprise an optical or radiation based positioning system.

The position or location tracking system may be configured to track a proximal end of the object or device and/or a reference point or part of the device. The location or position tracking system may be for determining a location or position of at least part of the object or device, such as a part of the object or device that is outwith a body and/or bone, e.g. in use.

The location or positioning tracking system may comprise an optical or other radiation based position or location tracking system, such as an Infra-red (IR) based location or position tracking system. The location or position tracking system may be configured to determine and/or track the position or location of the at least one reference point or part of the object or device. The reference point or part of the object or device may be or comprise or be provided on or with reference to a part of the object or device that is outwith the body and/or bone in use, e.g. a control or motor device, box or unit.

The location or position tracking system may comprise at least one base station and one or more tracked units. The base station may be fixed. The location or position tracking system may be configured to track the position of the one or more tracked units, e.g. relative to the base station. At least one of the one or more tracked units may be coupled to or mounted or provided on or in the object or device, which may be at the proximate end of the object or device, e.g. on or in the control system, control unit or another part of the device that is outside the body and/or bone in use, e.g. at the reference point or part. At least one of the one or more tracked units may be mounted on another medical or surgical device or tool.

The location or position tracking system, e.g. the base station and/or the one or more tracked units, may comprise at least one sensor, such as an optical or radiation sensor or detector, e.g. a camera. The location or position tracking system may be configured to track at least part of the device outside the drill hole, body and/or bone. The location or position tracking system, e.g. the base station and/or the one or more tracked units, may comprise at least one, and preferably two or more, radiation and/or light emitters and/or at least one radiation or light detector. The radiation and/or light emitter may comprise an LED, such as an infrared LED.

The radiation or light emitters may be configured to act as a stationary reference plane. The radiation or light emitters may be located on or attached to surgical objects and/or the device.

The radiation or light sensors or detectors may comprise a camera. For example, the cameras may be infrared cameras. The cameras may be configured or operable to provide 6 Degree of Freedom tracking information.

The light or radiation sensors or detectors may be or comprise a micro infrared camera. The tracked unit, e.g. on the object or device, may comprise two or more light or radiation sensors or detectors. The two or more light or radiation sensors or detectors may be interpolated. For example, light or radiation sensors or detectors may be interpolated to achieve a 1024×768 pixels configured to provide a frame rate up to 100 frames per second.

The location or position tracking system may be configured to determine and/or track the distance, angle and/or relative position of each tracked unit or detector and/or the part of the object or device associated therewith, e.g. by detecting, monitoring or sensing light or radiation emitted by the radiation and/or light emitter(s) of the base station and/or one or more tracked units, for example by using the light or radiation sensors or detectors of the one or more tracked units and/or the base station.

The base station may be stationary. The base station may be located remotely from the tracked unit(s). The base station may comprise at least one camera. The base station may comprise two or more radiation and/or light emitters. The base station may comprise or be configured to communicate with the processing device.

The base station may be configured to communicate with the tracked units. The communication may comprise wireless communication. The communication may be via a link. The communication may be via a high speed, low power radio-frequency link. The communication may be via a transceiver link.

The tracked units, which may be located on or attached to the surgical equipment and/or the object or device, may be configured to communicate with the base station in a sequenced fashion. The tracked units may be configured to communicate with the base station in a pulse coded fashion.

The radiation or light detector of each tracked unit may be configured to receive and/or record signals emitted by the one, two or more radiation and/or light emitters of the base station. The tracked units may each comprise a tracked unit processor. The tracked unit processor may be configured to determine the location or position of the tracked unit, e.g. based on the signals emitted by the one, two or more radiation and/or light emitters of the base station, which may be received by the radiation or light detector of the tracked unit. Each tracked unit may be configured to transmit or stream its location, e.g. according or relative to the reference frame, for example a coordinate system, which may be centred or based on the base station. Each tracked unit may be configured to transmit or stream its location through the wireless link. Each tracked unit may be configured to transmit or stream its location with a unique ID.

The camera of the base station may be configured to receive and/or record signals emitted by the one, two or more radiation and/or light emitters of at least one or each tracked unit, e.g. located on or attached to surgical equipment and/or the device. The base station may comprise or be configured to communicate with a base station processor, which may be, or be implemented by or comprised in the processing device. The base station processor may be configured to determine the position of at least one or each tracked unit, e.g. according to the reference frame, for example a coordinate system. The coordinate system may use the location of the base station as the reference location.

The base station processor may be configured to determine the position, which may be a 3D position, of one or more or each tracked unit with reference to the base station, e.g. based on the signals emitted by the one, two or more radiation and/or light emitters of the respective tracked units, which may be received by the radiation or light detector of the base station. The base station processor may use the position and/or location of the one or more or each tracked unit, e.g. the coordinates of the one or more or each tracked unit, determined by the base station processor and/or the one or more or each tracked unit processor to determine the position, e.g. the 3D position, of the one or more or each tracked unit with respect to the base station. The base station processor and/or tracked unit processor(s) may be configured to send location coordinates to the processing device. It will be appreciated that the processing device may be comprised in the location or position tracking system and/or be remote from the location or position tracking system, e.g. it may be server based or distributed. Furthermore, one or more or each of: the processing device, the base station processor and/or the tracked unit processor may be implemented by the same processing system or by different processing systems.

According to a sixth aspect of the present invention is a computer program product for controlling or at least partially implementing the device of the first aspect and/or the location or tracking system of the fifth aspect. For example, the computer program product may be configured to at least partially implement the navigation system, modelling system, mapping system and/or tracking system described above in relation to the first aspect and/or the method of the second aspect and/or the location or tracking system of the fifth aspect.

The computer program product may be provided on a carrier-medium, such as a non-transient and/or tangible carrier medium. The computer program product may be programmed or programmable into a processor and/or provided on a memory or storage, such as a RAM, ROM, on a hard drive, on a memory card, USB memory storage, a flash drive or card, and/or the like.

According to a seventh aspect of the present invention is a processing system, which may be comprised in a control unit for the device of the first aspect, when programmed with the computer program product of the sixth aspect. The processing system may comprise a processor. The processing system may comprise or be configured to access at least one data storage or memory. The processing system may comprise one or more communications systems, such as a wireless and/or network communication system, It will be appreciated that features analogous to those described in relation to any of the above aspects may be individually and separably or in combination applicable to any of the other aspects.

Apparatus features analogous to, or configured to implement, those described above in relation to a method and method features analogous to the use and fabrication of those described above in relation to an apparatus are also intended to fall within the scope of the present invention.

BRIEF DESCRIPTION OF THE FIGURES

Embodiments of the present invention will now be described, by way of example only, with reference to the accompanying drawings, which are.

DETAILED DESCRIPTION OF VARIOUS EMBODIMENTS

Figure 1:
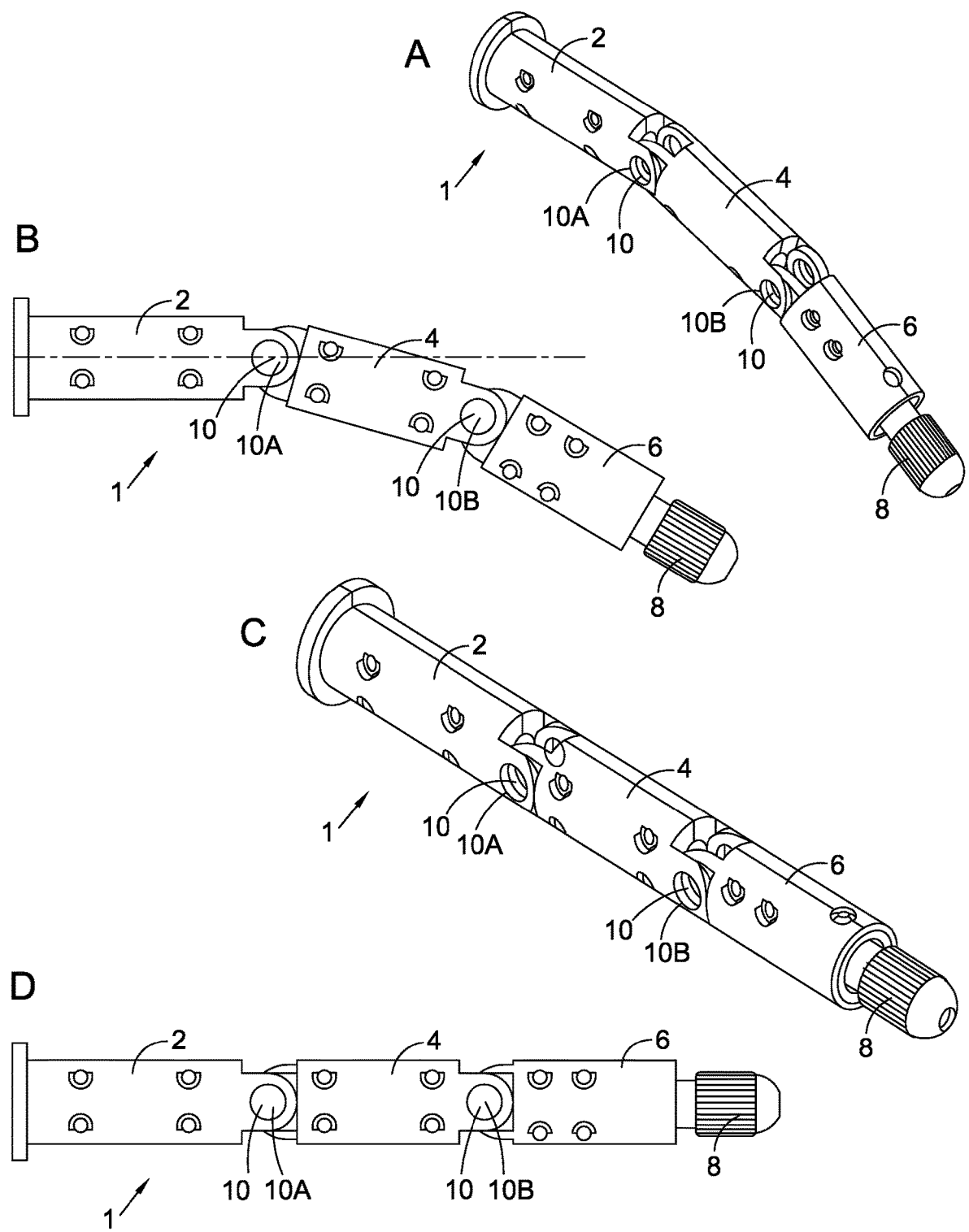
FIG. 1A: a perspective view of a drill arm in an example of a bent configuration.
FIG. 1C: a perspective view of the drill arm of FIG. 1A in a completely extended configuration.
FIG. 1B: a side view of the drill arm of FIG. 1A in the example of a bent configuration.
FIG. 1D: a side view of the drill arm of FIG. 1A in the completely extended configuration.

FIG. 1A shows a perspective view of a drill arm 1 for a surgical drill in a bent configuration. The drill arm 1 is configured to fit within a small incision in a bone that is to be drilled, for example a femur, tibia, fibula, patella, sinuses, neck bones, buccal bones, skull bones, and the like. A drill chuck 8 is provided on a distal end of the drill arm 1.

The drill arm 1 comprises a plurality of (in this example three) links 2, 4 and 6, which form a kinematic chain. A proximal or anterior end of a first link 2 is connected to a control box (not shown). A distal or posterior end of the first link 2 is connected via a joint 10a to a proximal or anterior end of a second link 4. A distal or posterior end of the second link 4 is connected via a joint 10b to a proximal or anterior end of a third link 6. A distal or posterior end of the third link 6 is connected to the drill chuck 8. It will be appreciated that links 2 and 6 are singular links and link 4 is a binary link. The links 2, 4 and 6 are rigid and hollow and are configured to accommodate or host a flexible shaft (not shown) for operating or driving the drill bit. For example, each link may take the form of a hollow metallic tube or cylinder comprised of suitable surgical grade metal or some other suitable rigid bio-compatible material. The joints 10 are configured to allow free rotation of the joint and may comprise any suitable joint, such as rivets. Each link 2, 4, 6 comprises one or more bearings (not shown) between the links 2, 4, 6 and the flexible shaft. For example, the bearings may be high-speed micro ball bearings.

In this way, the drill arm 1 is configured to act as a flexible sheath for the flexible shaft with the drill bit attached at the distal end of the drill arm 1. The drill arm 1 may be steered by means of wires (not shown), providing wire-driven steering capability. For example, the wires may run inside the links 2, 4, 6 of the arm 1. One end of each of the wires is attached to the distal end (i.e. the end comprising the drill bit) of the drill arm 1 and an opposite end of each of the wires is attached to a motor and/or actuator (not shown) for operating (i.e. paying out or retracting) the wires. The arm 1 is configured to be actuated by actuating the distal or furthermost link 6. Bending the distal or furthermost link causes the other links 4 and 2 to follow its movement. As such, links 4 and 2 are passively actuated and link 6 is actively actuated.

Figure 2:
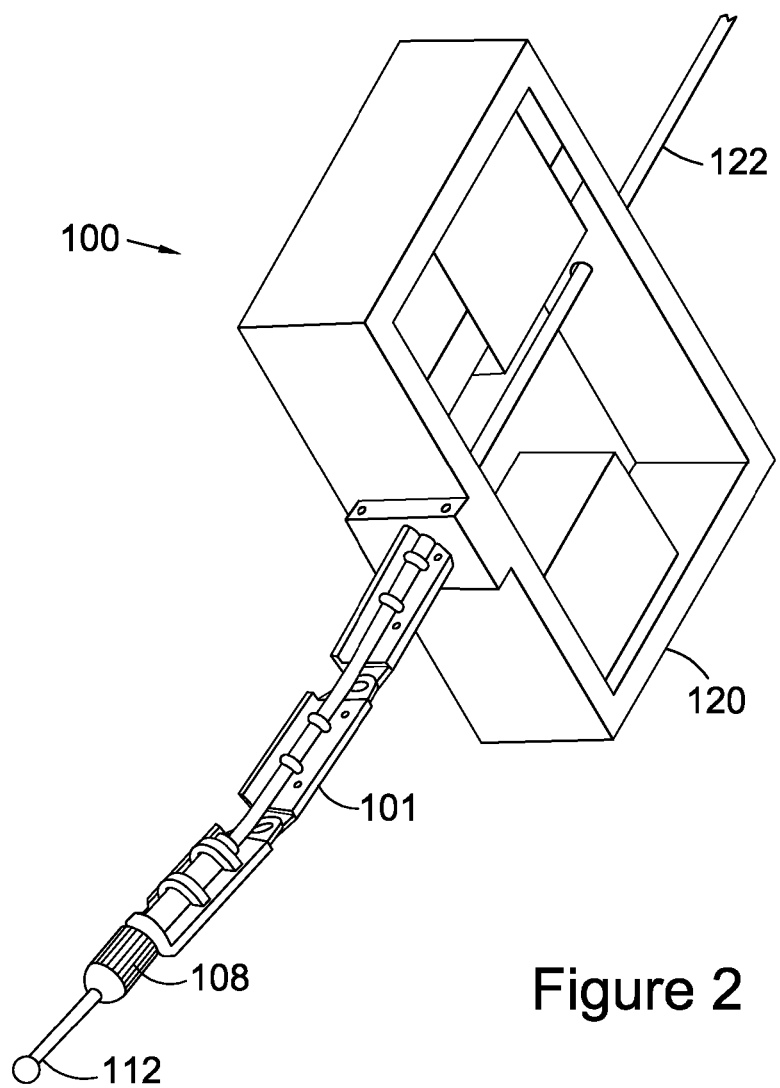
FIG. 2: a perspective view of a surgical drill comprising the drill arm of FIG. 1A.

FIG. 2 shows a perspective view of another example of a surgical drill 100. The drill 100 comprises a drill arm 101, which is similar to the drill arm 1 shown in FIGS. 1A to 1D. A proximal end of the drill arm 101 is connected to a control box 120 and a distal end of the drill arm 101 is connected to a drill chuck 108. The drill chuck 108 is configured to hold a drill bit 112. The drill arm 101 is hollow and hosts a flexible shaft 122 in its cavity. The flexible shaft 122 is connected to a motor (not shown), such as a servo motor. The motor is configured to operate the drill bit 112 and cause it to rotate at the required speed. The motor can be of any suitable type, such as a servo motor or a high torque servo motor. Advantageously, a high torque servo motor can allow sustained bending of the drill arm while maintaining the bone milling/drilling action.

Figure 3:
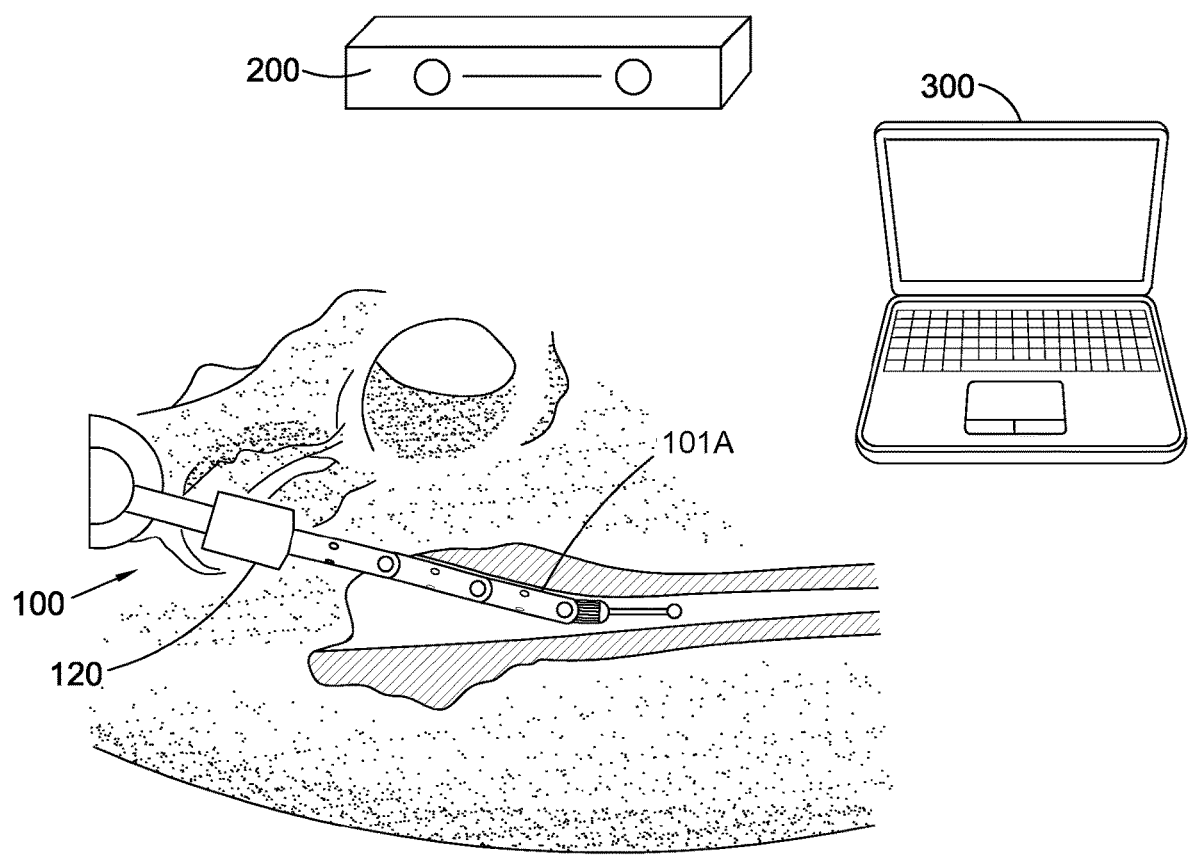
FIG. 3: a schematic representation of a system comprising the surgical drill of FIG. 2, a tracking system and a processor.

FIG. 3 shows a schematic representation of the surgical drill 100, in operation while drilling a hole in a bone. The drill arm 101A is inserted in a bone cavity of the bone at an appropriate angle for drilling the required shape, for example to enable insertion of a prosthesis, such as a femoral head. The drill arm 101A is connected to the control box 120, which acts as a motor housing. The drill 100 is operable using a tracking system 200 and processor 300, which in this embodiment is a computer. The drill arm 101A is configured to provide one or more degrees of freedom of movement while bending. Advantageously, this allows the drill arm 101A to navigate through the incision while drilling the bone. A twist or rotational motion of the drill arm 101A can be achieved manually, for example by twisting the control box 120. Alternatively or additionally, the twist or rotational motion of the drill arm 101A can be automated, for example by rotating the entire arm 101A from control box 120.

Figure 4:
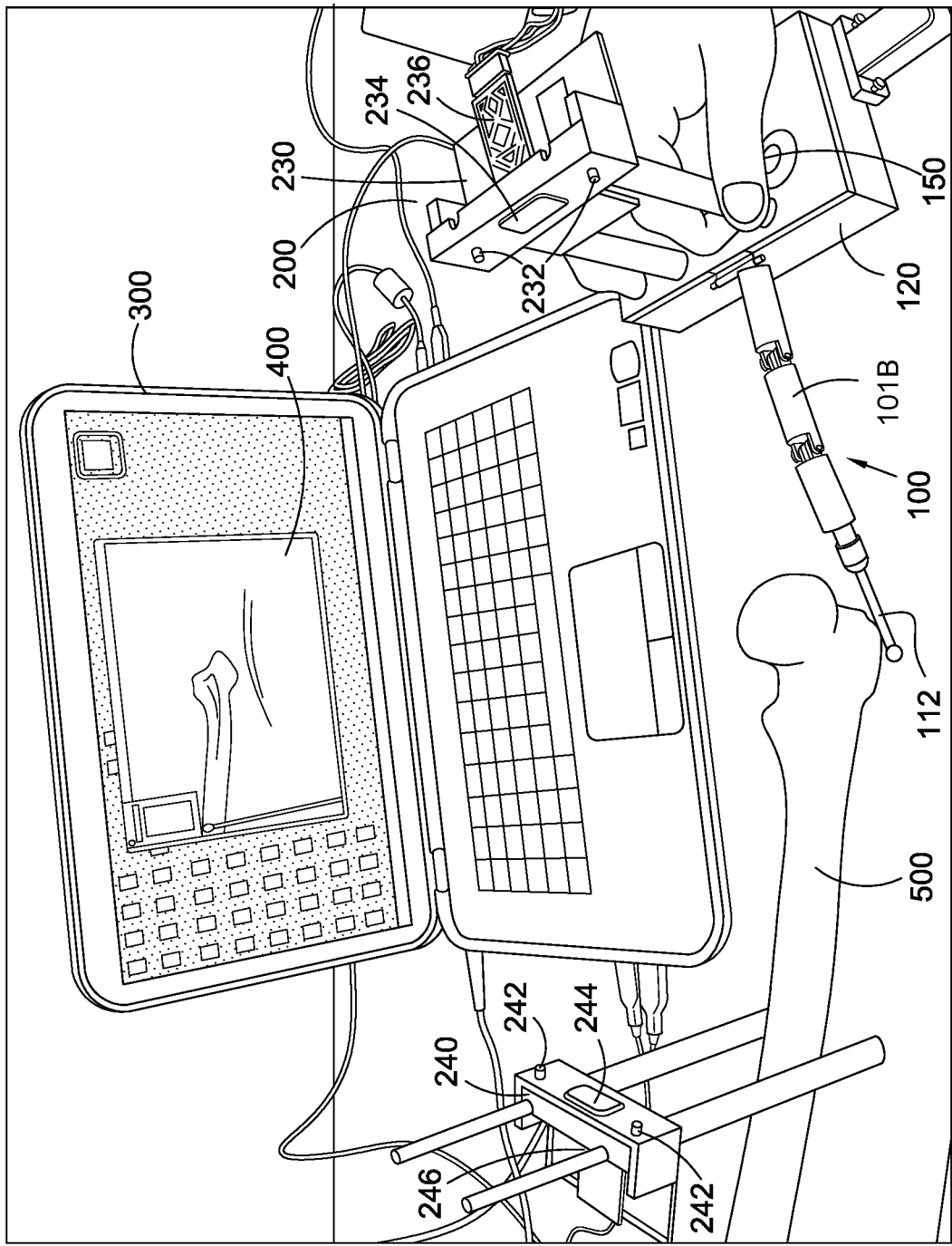
FIG. 4: a bone milling surgery set up employing the surgical drill of FIG. 2.

FIG. 4 shows a bone milling surgery system employing the surgical drill 100. The drill 100 is held manually by gripping the control box 120. In this instance, the flexible drill arm 101B comprises the drill arm 1 described in FIG. 1. The drill arm 101B is operated by means of an actuator 150, which in this case is a control stick. The actuator 150 enables the user, for example a surgeon, to steer the drill arm 101B and to bend it in a desired angle. The drill bit 112 of the drill 100 is brought into contact with a bone 500 in order to start the milling operation.

The drill 100 comprises an optical tracking system 200 configured to track the part of the drill 100 that is outside the drill hole. The tracking system comprises a base unit 240 and a drill tracking system 230 located on the drill 100. The base unit 240 is located remotely from the drill 100 and it is stationary. The base unit 240 is configured to act as a stationary reference plane. The base unit 240 comprises a camera 244, which can be any suitable type of camera, for example a micro infrared camera.

The base unit 140 also comprises two spaced apart light emitters 242, which can be any suitable type of light emitters, for example infrared LEDs. The base unit 240 also comprises a micro-processing unit 246.

The drill tracking unit 230 comprises a camera 234, which may be any suitable type of camera, for example a micro infrared camera. The drill tracking unit 230 also comprises two spaced apart light emitters 232, which may be any suitable type of light emitters, for example infrared LEDs. The drill tracking unit 230 also comprises a micro-processing unit 236.

The base unit 240 and the drill tracking unit 230 communicate with each other wirelessly, for example via a transceiver link. The base unit camera 244 is configured to monitor the light emitted by the light emitters 232 of the drill tracking unit 230 and the drill tracking unit camera 234 is configured to monitor the light emitted by light emitters 242. The base unit 240 and the drill tracking unit 230 are configured to stream their locations to each other according to a coordinate system. The information is transmitted in a pulse coded fashion with a unique 24 bit ID in order to avoid confusion during the exchange of information.

The drill tracking system micro-processing unit 236 is configured to determine the position of the base unit 240 and use this as the reference location to calculate the position of the drill tracking unit 230. The micro-processing unit 246 of the base unit 240 uses coordinates obtained from the location of the base unit 240 and the drill tracking unit 230 in order to determine the 3D position of the drill tracking unit 230.

The base unit's micro-processing unit 246 sends the location coordinates to a remote processor, in this case computer 300, which comprises software for displaying a virtual reality viewing system 400 in which the user, for example a surgeon, can observe a virtual model of the position of the drill 100 relative to the bone 500.

The drill 100 also comprises a non-optical tracking system in the form of a rotary encoder system configured to track the bending angle of each joint and the position of the drill arm 101B, and particularly the distal end of the drill arm 101B, with reference to the controller box 120. Each joint 10A, 10B of the drill arm is provided with a rotary encoder. The encoders comprise a potentiometer, such as a button potentiometer, that is configured to vary its voltage when the potentiometer rotates. The voltage output of each potentiometer at each degree of rotation is then related to the bending angle of the joints, for example by provision of a suitable map, look up table, algorithm and/or the like. For example, the potentiometer is configured to transmit analogue data to a controller (which may be the same as or different to the computer 300 or the drill tracking system micro-processing unit 236). The controller comprises an analogue to digital converter to convert the analogue data from the potentiometer into digital data. The geometrical properties of the drill arm 101B, e.g. the length and/or diameter or thickness or other dimensions or 3D profiles of each link 2, 4, 6, are predetermined and stored in a memory that is accessible by the controller. In this way, knowing at least the length of each link 2, 4, 6 and the angles of the joints 10A, 10B calculated using the rotary encoders, the 3D position of the drill arm 101B and particularly the location of the distal end of the drill arm 101B and thereby the position of the drill chuck 108 and the drill bit 112 can be calculated. For, example, the position of the distal end of the drill arm 101B with reference to the controller box 120 may be determined by forward kinematics.

Figure 5:
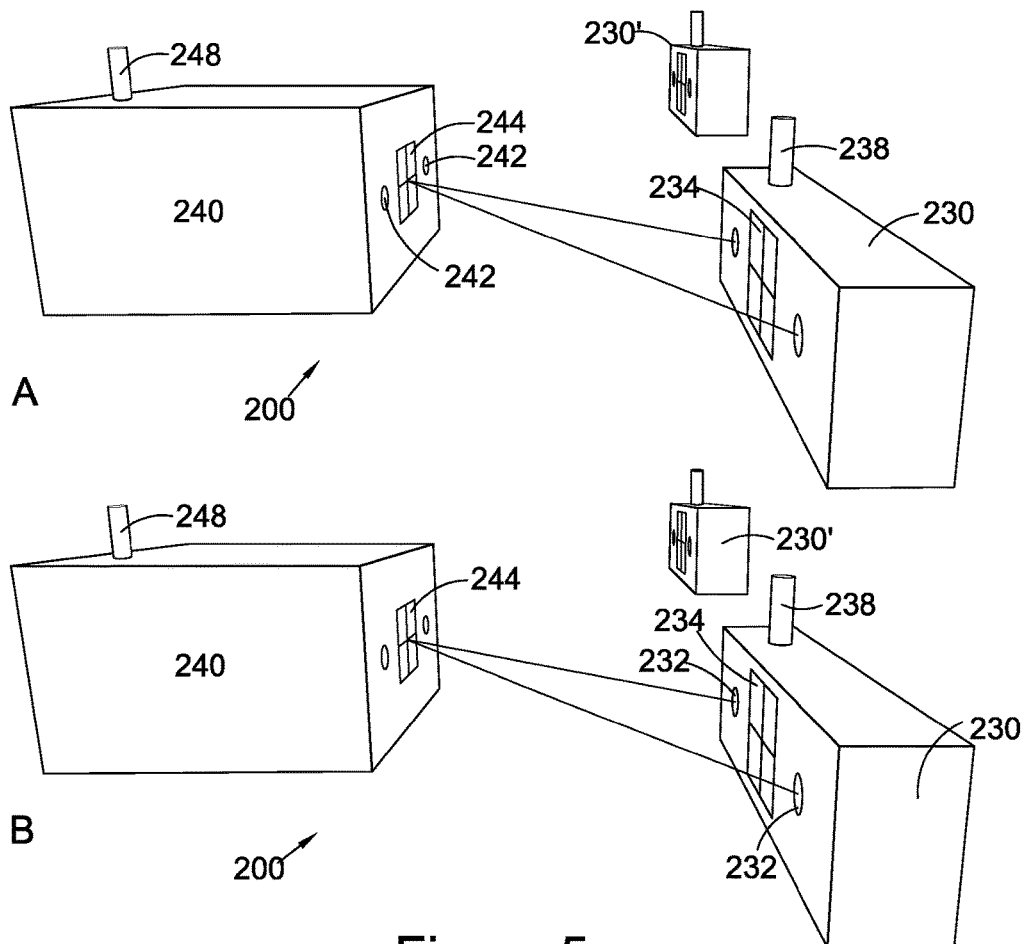
FIG. 5: schematic representations of the tracking system of the system of FIG. 3.

FIG. 5 shows a schematic representation of the optical tracking system 200. A tracking system base unit 240 comprises a pair of spaced apart light emitters 232a. The light emitters 232 are imaged by a camera 234 located on a first drill tracking unit 230. In this way, the image of the spaced apart pair of light emitters 232 on the base station collected by the camera 234 can be used to gather information on the reference location of base unit 240. A pair of spaced apart light emitters 232b are also provided on the first drill tracking unit 230. The light emitters 232b of the first drill tracking unit 230 are imaged by the base unit camera 244. The images of the spaced apart light emitters 232b of the first drill tracking unit from the camera 244 on the base unit can be processed in order to obtain the perspective coordinates of the first drill tracking unit relative to the base unit location. The sequence of information transfer is then repeated with a second drill tracking unit 230', which is structurally similar to the first drill tracking unit 230. Each drill tracking unit 230, 230' sends information to the base unit 240 in a pulsed fashion and with a unique 24 bit ID, in order to avoid mixing or muddling of data and to uniquely identify each tracking unit 230, 230'. The drill tracking unit's light emitters 232b are radio frequency linked to the base unit 240 by radiofrequency transceiver links 238 and 248 and the base unit 240 can sequentially turn on and off the light emitters 232b of each drill tracking unit 230, 230'.

Every set of coordinates obtained from the base unit 240 and the corresponding drill tracking unit 230, 230' provides two perspectives and with this information the base unit's micro-processing unit then calculates the 3D position of each drill tracking unit and correlates it to their respective locations. The base unit 240 acts as the origin for the entire tracking system. The drill tracking units 230, 230' can be provided at different locations on the drill 100 or on different surgical tool used in a procedure, for example, and can thereby be used to track the position and configuration/conformation of the drill 100 and particularly the drill arm 101.

The base unit 240 serially sends the calculated coordinate data to a remote processor, for example the computer 300, which can use the coordinate information to produce a virtual reality viewing system to guide the user in the milling operation. In this embodiment, the remote processor 300 is configured to receive and process coordinate data but not image data. Processing coordinate data is faster than processing image data and therefore, the remote processor 300 is configured to accommodate high tracking rates with low system memory usage and low jitter.

Figure 6:
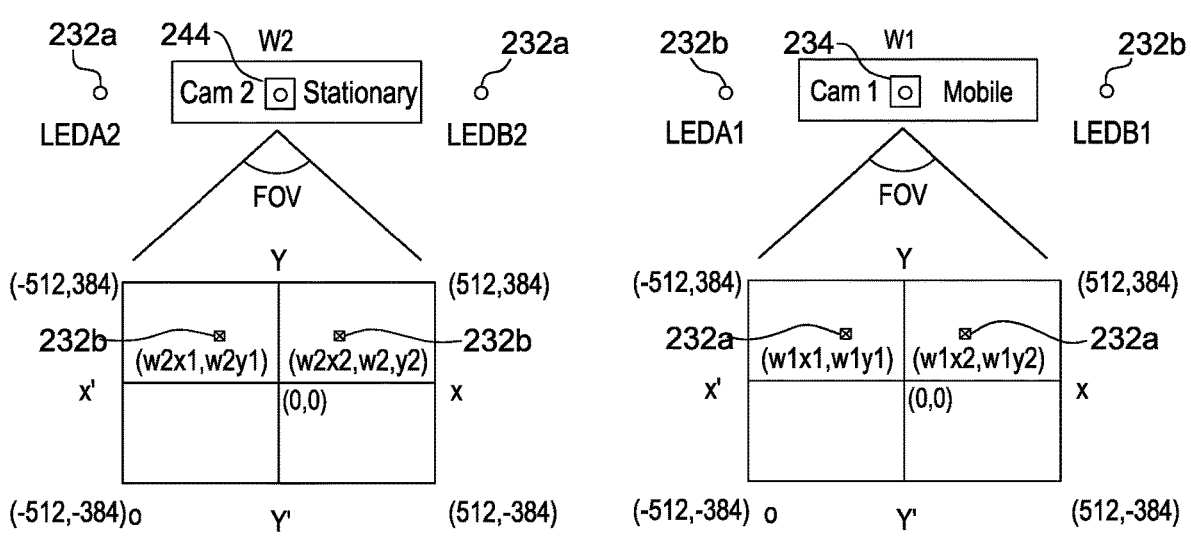
FIG. 6: a representation of two perspective coordinate images obtained by the tracking system of FIGS. 5A and 5B.

FIG. 6 shows a representation of two perspective coordinate images obtained by a tracking system as described above, wherein the left hand schematic of FIG. 6 shows the image of the light emitters 232b of one of the drill tracking units 230, 230' taken by the camera 244 of the base unit 240, whilst the right hand schematic of FIG. 6 shows the image of the light emitters 232a of the base unit 240 taken by the camera 234 of the drill tracking unit 230, 230'. The relative X, Y and Z coordinates of an object can be easily calculated from any two perspective images, using principles of perspective geometry.

Since each base tracking unit 240—drill tracking unit 230, 230' pair forms a closed loop and the light emitters 232a, 2332b are pulse encoded, there cannot be any confusion in tracking drill tracking units 230, 232' even if they are closely placed, as in the case of ultrasound guided surgeries or single port, laparoscopic and arthroscopic surgical units in conjunction with virtual reality. The use of a tracking system as described above would give the surgeon information about the 3D location and orientation of the surgical tools, such as the surgical drill 100 and make the process of navigated surgery much easier and more reliable, even when the tools are close to each other. Potential applications of this tracking system technology can also be applied in hybrid systems such as laparoscopy tracking with virtual reality or ultrasound tracking with multimodality tracking and navigation.

Figure 7:
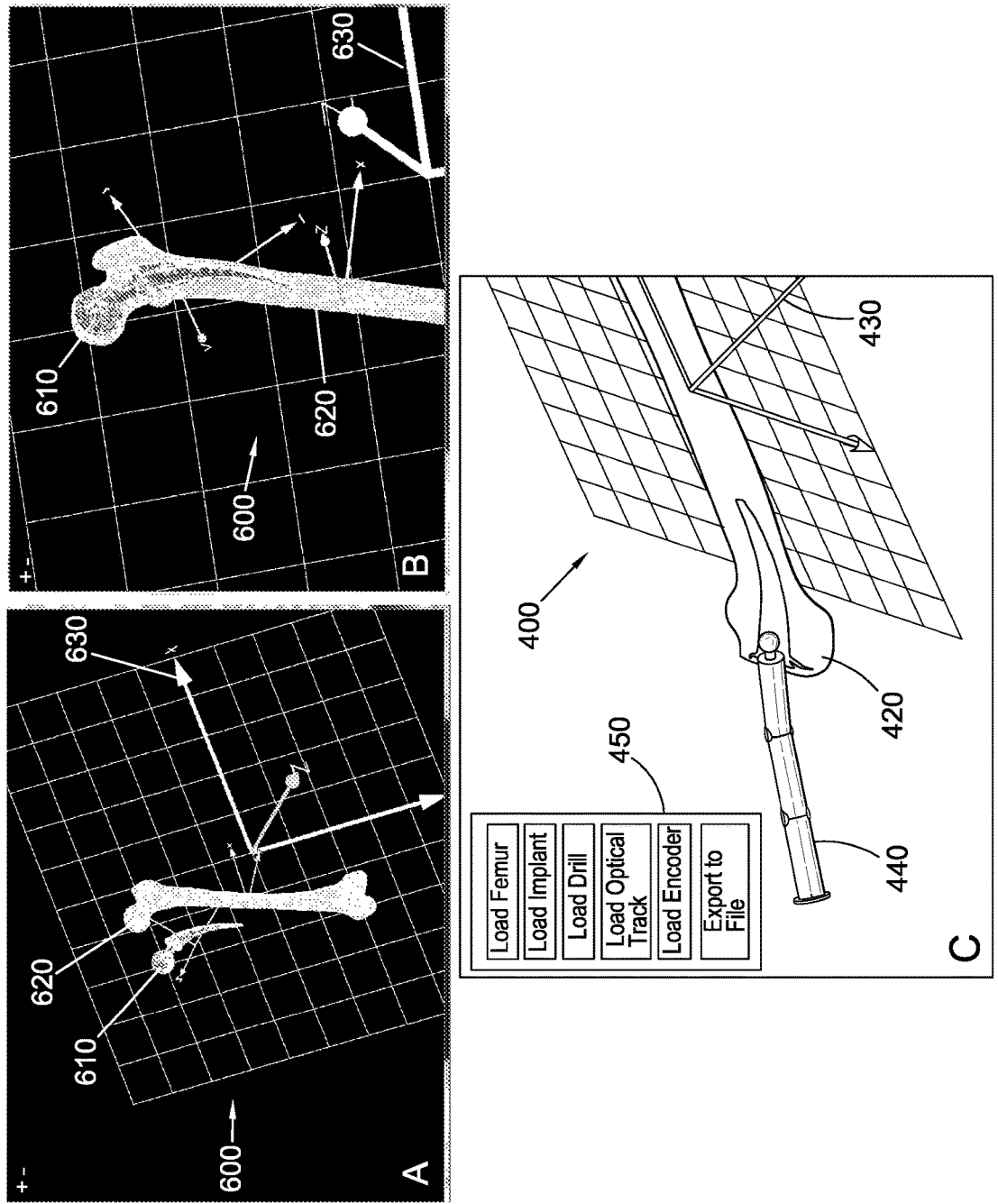
FIG. 7A: a 3D model comprising a femur and a femoral stem implant used by the system of FIG. 3.
FIG. 7B: the 3D model of FIG. 3 with the implant inserted in the femur.
FIG. 7C: a user interface of the system of FIG. 3.

FIG. 7A shows a 3D mapping system 600 that maps a bone, in this case a femur 620, and an implant, such as a femoral stem implant 610, wherein FIG. 7A shows the femur 620 and femoral stem implant 610 prior to insertion of the implant 610 into the bone 620. The mapping system 600 creates a virtual operating space in which virtual objects, corresponding to objects from the surgical procedure, can be moved. In this case, the virtual objects comprise models of the bone 620, the implant 610 and the drill 100, e.g. the drill arm 101 and the drill bit 112. The models could be obtained by acquiring a 3D CAD image of the respective objects, such as the bone 620 and the implant 610. These could be obtained, for example, from a CT scan of said objects. The CT scan data can be imported in "xyz-cood" format into software such as MESHLAB. The virtual object environment for mapping can be programmed in JAVA and can comprise one or more virtual objects at the same time. Once imported, the virtual objects can be moved, rotated and/or overlapped with other objects within the virtual operating space.

FIG. 7B shows the 3D mapping system 600 with the femoral stem implant 610 inserted into the femur 620, i.e. with the virtual models of the implant 610 and the bone 620 overlapping. The XYZ axes 630 represents a coordinate system used to position the virtual models in both FIGS. 7A and B.

The mapping system 600 implements a boundary representing a safe surgical volume that can be milled. Placing the implant model 610 in the final location within the femur model 620 can be used to establish the boundary of the safe surgical volume to be milled, that is, for example, the volume confined to the implant model 610. During milling operation, the mapping system 600 is configured to monitor the position of the drill bit 112 with respect to the boundary of the safe surgical volume and to restrict the drill motor and cause it to stop when the drill bit 112 reaches the boundary or at least within a threshold distance thereof.

FIG. 7C shows a navigation system 400 with a virtual tool 440, a virtual bone model 420, XYZ axes 430 and surgical planning tool 450. The navigation system 400 operates in combination with the mapping system 600 above and employs hybridisation of the optical tracking system as detailed above with the rotary encoder tracking system. The optical tracking system (for example the optical tracking system 200 described above) is used to track the surgical objects outside the drill hole, while the rotary encoders located at the joint 10A, 10B between each link 2, 4, 6 of the drill arm 101 are used to track the end of the drill bit 112 once it is inserted in the drill hole and no longer visible by the optical tracking system 200. The rotary encoders provide bending or rotation angle data of each link 2, 4, 6 relative to the preceding link 2, 4, 6. The bending or rotation angle data, combined with the length of each link is then used to map the position of drill arm 101 and synchronise it with its virtual object.

Figure 8:
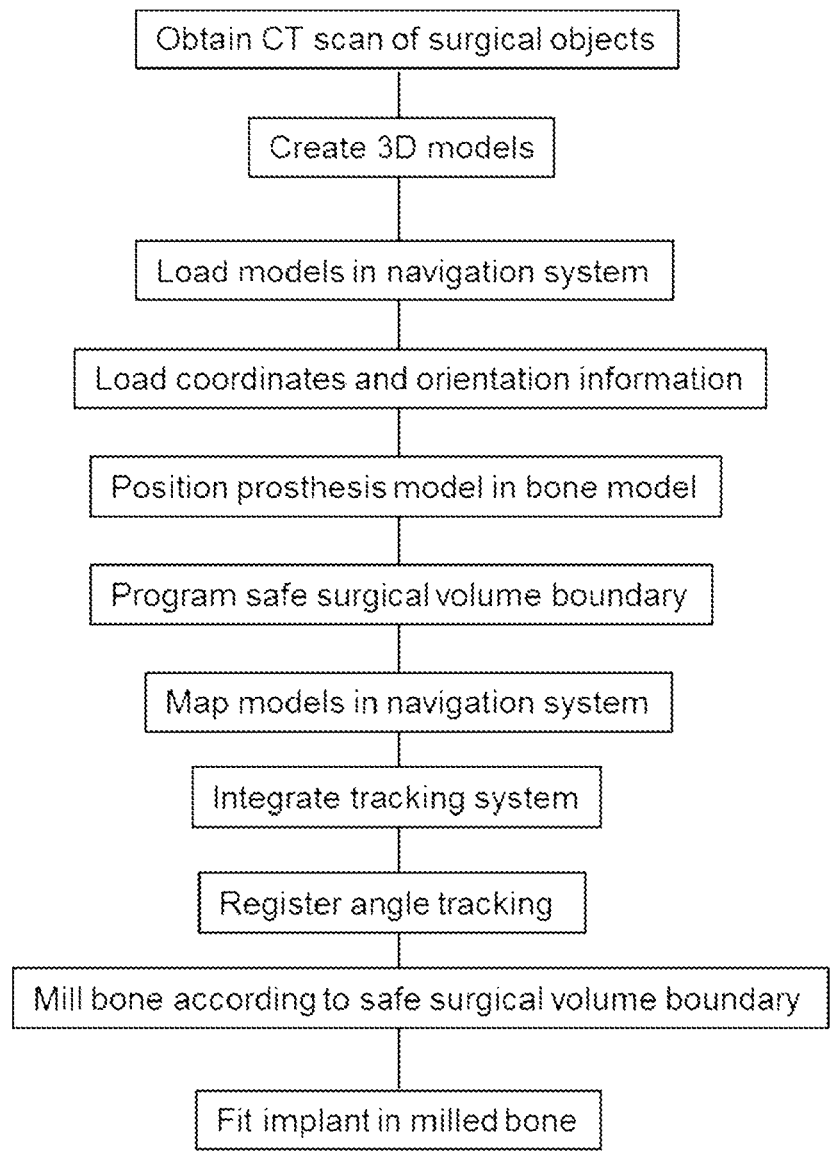
FIG. 8: a flowchart of a method of drilling or milling a bone using the system of FIG. 3.

FIG. 8 shows the steps of a method of drilling or milling a bone according to the invention. The method comprises obtaining a CT scan of the surgical objects involved in the method/procedure, such as the bone 620 to be drilled and the corresponding implant 610. The CT scan data is used to create 3D models of the scanned objects, that can then be loaded, along with their location coordinates and orientation information, into the navigation system. The method further comprises positioning the prosthesis model in the bone model and deriving and programming a safe surgical volume boundary thereby. The models are mapped in the navigation system. The tracking system monitors the angle of the joints 10A, 10B of the drill arm 101 of the surgical drill using the rotary encoders along with the position of a reference point of the drill 100 that is outwith the body using the optical tracking system during milling of the bone and updates the position of the virtual model drill bit 112 and the model of the bone 620 (i.e. to reflect the milling). The position of the drill bit 112 is also compared to the calculated safe surgical volume boundary and the drill motor moderated or stopped when the boundary is reached or approached. The model also monitors fitting the implant in the milled bone.

It should be understood that the embodiments described are merely exemplary of the present invention and that various modifications may be made without departing from the scope of the invention.

It should also be understood that references herein to drilling a bone or other body parts need not be limited to drilling the bone or other body parts during a surgical procedure but may comprise other non-surgical applications such as performing a post-mortem or scientific analysis or procedure, during manufacture of an object such as a prosthesis or teaching or educational aid and/or the like. Indeed, although the description above refers to surgical tools, it will be appreciated that the present invention is also equally applicable to non-surgical remote operations tools such as remote inspection tools, e.g. for inspecting inside pipes and other hard to access places, robotic arms and/or the like.

The invention claimed is:

1. A remote operations surgical system, the remote operations surgical system comprising:

a surgical instrument having an arm and either a tool or a load, the arm comprising at least three segments, the at least three segments being at least three links of a kinematic chain, at least two of the three segments being selectively reconfigurable relative to one or more other segment of the three segments, the at least two of the three segments being configured for insertion into a body;

a hybrid position tracking system that comprises a single non-optical or non-radiation-based position tracking system and a single optical or radiation-based position tracking system that are collectively configured to determine or track a position of the surgical instrument in use when inside the body; and a processing device in communication with at least the non-optical or non-radiation-based position tracking system, wherein:

the non-optical or non-radiation-based position tracking system comprises two bend, rotation, or angular sensors for measuring a relative angle or orientation between the three segments of the arm, is an extension of the optical or radiation-based position tracking system, and is configured to track a distal end of the arm relative to a proximal end of the arm, the distal end of the arm being provided with the tool or the load, the proximal end of the arm being an opposite end of the arm relative to the distal end of the arm on which the tool or the load is located;

the optical or radiation-based position tracking system comprises at least one base station and one or more tracked units, the optical or radiation-based position tracking system being configured to determine or track a position of the one or more tracked units relative to the base station at least one of the one or more tracked units being coupled to and fixedly mounted at the proximal end of the arm of the surgical instrument such that movement of the proximal end of the arm results in movement of the one or more tracked units and the position of the proximal end of the arm of the surgical instrument is determined or tracked by the optical or radiation-based position tracking system;

each of the two bend, rotation, or angular sensors are located at a respective joint between the three segments of the arm;

the three segments are located between the tool or load and the at least one of the one or more tracked units coupled to and fixedly mounted at the proximal end of the arm, such that the non-optical or non-radiation-based position tracking system is operable to track the position of the distal end of the arm with reference to the proximal end of the arm;

the remote operations surgical system implements or communicates with a navigation system for facilitating navigation or operation of the remote operations surgical system using the position obtained from or using the non-optical or non-radiation-based position tracking system and the optical or radiation-based position tracking system;

the processing device is configured to determine the position of the distal end of the arm using a measured relative angle or position of the three segments of the arm, the processing device further comprising a modelling system that creates a virtual model of at least part of the surgical instrument and one or more other objects, tools or devices, positions used by the virtual modelling system comprising the positions able to be determined or tracked by the non-optical or non-radiation-based position tracking system and the optical or radiation-based position tracking system; and movement of at least one of the surgical instrument or the one or more other objects, tools or devices via the navigation system is based upon the virtual model created by the processing device modelling system.

2. The remote operations system according to claim 1, wherein:

the tool or the load comprises a bone drill bit, and the arm is configured for insertion into a bone of the body.

3. The remote operations surgical system according to claim 1, wherein at least one of the bend or angular sensors comprises a potentiometer or is configured to provide at least one of a variable voltage or resistance that depends on a relative angle between two connected or adjacent segments.

4. The remote operations surgical system according to claim 1, wherein the optical or radiation-based position tracking system is further configured, in use, to determine a position of at least part of the arm that is outside of the body or a bone of the body.

5. The remote operations surgical system according to claim 1, wherein at least one of the one or more tracked units is mounted or provided or in a control system, control unit, or another part of the surgical instrument that is outside at least one of the body or a bone in use or at a reference point or part.

6. The remote operations surgical system according to claim 1, wherein:

the one or more tracked units comprises at least one optical or radiation sensor or detector;

the base station comprises at least one radiation or light emitter;

at least one of the one or more tracked units comprises a tracked unit processor, the tracked unit processor being configured to determine a position of the tracked unit based on signals emitted by the at least one radiation or light emitter of the base station, the signals being received by the radiation or optical detector of the tracked unit;

the base station comprises at least one optical or radiation sensor or detector and the one or more tracked units comprises at least one radiation or light emitter;

the base station is configured to communicate with a base station processor; and the base station processor or the processing device is configured to determine a position of the at least one of the one or more tracked units based on signals emitted by the at least one radiation or light emitter of the at least one of the one or more tracked units that are received by the radiation or optical detector of the base station.

7. The remote operations surgical system according to claim 6, wherein the remote operations surgical system is configured to determine or track at least one of a distance, angle or relative position of each detector or part of the surgical instrument associated therewith by detecting, monitoring or sensing light or radiation emitted by the at least one radiation or light emitter of the base station or the one or more tracked units using the light or radiation sensors or detectors of the one or more tracked units or the base station.

8. The remote operations surgical system according to claim 6, wherein the base station is configured to communicate with the tracked units using wireless communication.

9. The remote operations surgical system according to claim 8, wherein the tracked units are configured to communicate with the base station in at least one of a sequenced fashion or a pulse coded fashion.

10. The remote operations surgical system according to claim 6, wherein at least one of the tracked units are configured to transmit or stream their location through a wireless link.

11. The remote operations surgical system according to claim 6, wherein:
the position of one or more tracked units determined by the processing device is used to determine the position of the at least one tracked unit with respect to the base station.

12. The remote operations surgical system according to claim 11, wherein:
the base station processor or the processing device is configured to implement:
the navigation system; and
a mapping system for determining relative positions of at least part of the surgical instrument or a part of a patient or at least one other medical or surgical object; and
the navigation system or the mapping system is configured to use the position of the surgical instrument determined by the non-optical or non-radiation-based position tracking system and the optical or radiation-based position tracking system to at least one of:
track, steer, move or maneuver at least part of the surgical instrument; or
determine the relative positions of the at least part of the surgical instrument or the part of a patient or the at least one other medical or surgical object.

13. The remote operations surgical system according to claim 12, wherein the base station processor or the processing device is configured to implement or provide at least one of a viewing system or a display or a virtual reality viewing system or a man-machine interface.

14. The remote operations surgical system according to claim 13, wherein the viewing system or display or man-machine interface is configured to display the position of the surgical instrument relative to the position of the one or more other objects, tools or devices based on the positions determined using at least one of the modelling system or the non-optical or non-radiation-based position tracking system and the optical or radiation-based position tracking system.

15. The remote operations surgical system according to claim 12, wherein the modelling system is configured to at least one of produce or update the virtual model based on the position of the surgical instrument determined or tracked by the non-optical or non-radiation-based position tracking system and the optical or radiation-based position tracking system or geometric properties or dimensions or a 3D geometrical description of the surgical instrument or of the one or more other objects, tools or devices.

16. The remote operations surgical system according to claim 12, wherein the modelling system is configured to update the virtual model in real time or near real time during a procedure.

17. The remote operations surgical system according to claim 12, wherein at least one of the hybrid position tracking system or the mapping system is configured to use the virtual model in order to at least one of track, move or map the surgical instrument or the one or more other objects, tools or devices.

18. The remote operations surgical system according to claim 17, wherein at least one of the navigation system, a viewing system, display, or man-machine interface is configured to guide a surgical procedure by providing at least part or all of the model from the modelling system in real time.

19. The remote operations surgical system according to claim 12, wherein the navigation system is configured to create a virtual milling pattern in the virtual model of the at least one other object in use, and the surgical instrument is movable or articulatable or reconfigurable according to the virtual milling pattern.

20. The remote operations surgical system according to claim 12, wherein the mapping system is at least one of configured or programmable to provide, set up or monitor a boundary of safe surgical volume, and the mapping system is configured to at least one of display a warning message or stop a motor configured to operate the tool or the load, or stop or change operation of the tool or the load when the tool or the load reaches or approaches within a threshold limit of the boundary.

21. A method of drilling or milling with the remote operations surgical system of claim 1, the method comprising the step of reconfiguring the arm of the surgical instrument of the remote operations surgical system during drilling or milling based on the virtual model based on the position of the surgical instrument determined or tracked by the non-optical or non-radiation-based position tracking system and the optical or radiation-based position tracking system.

22. The method of claim 21, wherein the method comprises pre-operative planning computer assisted orthopaedic surgery (CAOS) comprising the step of mapping virtual models of at least one of a bone or a prosthesis into the navigation system.

23. The method of claim 21 further comprising the steps of:
providing the virtual model of the surgical instrument to the navigation system; and
obtaining a position of the arm of the surgical instrument or the tool or the load from or using the non-optical or non-radiation-based position tracking system and the optical or radiation-based position tracking system of the surgical instrument during the drilling or milling.

24. The method of claim 21, further comprising the step of registering the virtual model with an associated device or object using the optical or radiation-based position tracking system, wherein the associated device or object comprises at least one of: the surgical instrument, bone or prosthesis.

25. The method according to claim 21, further comprising the step of milling the bone according to a safe surgical volume boundary and providing at least one of a warning or an indication stopping or changing operation of a drill motor when a drill bit reaches or touches a boundary.

26. The remote operations surgical system according to claim 1 further comprising a computer program product comprising a non-transitory computer readable medium having computer program instructions stored therein, said computer program instructions being configured to cause the computer program product to control or at least partially implement the remote operations surgical system of claim 1 when executed by the processing device.

27. The remote operations surgical system according to claim 26 further comprising a distributed processing system for use with the computer program product of claim 26, the distributed processing system comprising a wireless or networked communication system and the processing device, the distributed processing system being configured to, via the wireless or networked communication system, access at least one data storage or memory on which the computer program is stored.

28. The remote operations surgical system of claim 1, wherein the arm of the surgical instrument has a maximum diameter of less than 10 mm.

29. The remote operations surgical system of claim 1, further comprising at least one moving or actuating mechanism for moving at least two of the three segments relative to the at least one or more other segment of the three segments.

30. The remote operations surgical system of claim 29, wherein the at least one moving or actuating mechanism comprises one or more control members, wherein one end of the one or more control members is connected to the corresponding segment, and wherein the one or more control members are flexible control members.

31. The remote operations surgical system of claim 30, wherein at least one of:
the end of the one or more flexible control members is connected to the segment at the distal end of the arm such that the arm is configured to be actuated by actuating the segment at the distal end of the arm; or
the segments are hollow and are configured to accommodate the one or more flexible control members such that the one or more control members run within at least one or more or each of the hollow segments.

32. The remote operations surgical system of claim 30, wherein an opposite end of the one or more flexible control members is connected to a motor or actuator for operating the one or more flexible control members.

33. The remote operations surgical system of claim 1, wherein the at least three links of the kinematic chain defining the at least three segments comprise at least one binary link and at least two singular links.

34. The remote operations surgical system of claim 1, wherein each respective joint between the three segments of the arm comprises revolute joints, such that each of the at least three links of the kinematic chain defining the at least three segments is configured to be rotated with respect to the other of the at least three links.

35. The remote operations surgical system of claim 1, wherein each of the at least three links of the kinematic chain is hollow.

36. The remote operations surgical system of claim 1, wherein each of the at least three links of the kinematic chain is cylindrical.

37. The remote operations surgical system of claim 1, wherein each of the at least three links of the kinematic chain have a predetermined length, wherein the processing device is configured to determine the position of the distal end of the arm, the tool or load based on the measured relative angle between links of at least one or each pair of adjacent links and the length of at least one link.

38. The remote operations surgical system of claim 1, wherein each of the two bend, rotation, or angular sensors comprise rotary encoders.

* * * * *

UNITED STATES PATENT AND TRADEMARK OFFICE
CERTIFICATE OF CORRECTION

PATENT NO. : 11,806,082 B2
APPLICATION NO. : 15/580825
DATED : November 7, 2023
INVENTOR(S) : Wei Yao et al.

It is certified that error appears in the above-identified patent and that said Letters Patent is hereby corrected as shown below:

In the Claims

In Column 22, Line 13, Claim 2, delete "operations system" and insert -- operations surgical system --, therefor.

Signed and Sealed this
Thirteenth Day of February, 2024

Katherine Kelly Vidal
*Director of the United States Patent and Trademark Office*